United States Patent
Chen et al.

(10) Patent No.: US 11,478,163 B2
(45) Date of Patent: Oct. 25, 2022

(54) IMAGE PROCESSING AND EMPHYSEMA THRESHOLD DETERMINATION

(71) Applicant: Neusoft Medical Systems Co., Ltd., Liaoning (CN)

(72) Inventors: Lei Chen, Liaoning (CN); Qiang Li, Liaoning (CN); Yan Kang, Liaoning (CN)

(73) Assignee: Neusoft Medical Systems Co., Ltd., Liaoning (CN)

( * ) Notice: Subject to any disclaimer, the term of this patent is extended or adjusted under 35 U.S.C. 154(b) by 593 days.

(21) Appl. No.: 16/569,227

(22) Filed: Sep. 12, 2019

(65) Prior Publication Data
US 2020/0085344 A1  Mar. 19, 2020

(30) Foreign Application Priority Data

Sep. 14, 2018  (CN) .......................... 201811073199.5

(51) Int. Cl.
*A61B 5/08* (2006.01)
*A61B 5/00* (2006.01)
(Continued)

(52) U.S. Cl.
CPC ................ *A61B 5/08* (2013.01); *A61B 5/004* (2013.01); *A61B 5/746* (2013.01); *G06K 9/6226* (2013.01);
(Continued)

(58) Field of Classification Search
CPC .......... A61B 5/08; A61B 5/004; A61B 5/746; G06K 9/6226; G06K 9/6218; G06N 7/005;
(Continued)

(56) References Cited

U.S. PATENT DOCUMENTS

| | | | |
|---|---|---|---|
| 2007/0127802 A1 | 6/2007 | Odry et al. | |
| 2011/0280457 A1* | 11/2011 | Nielsen | G06T 7/0012 |
| | | | 382/128 |
| 2016/0203263 A1* | 7/2016 | Maier | G16H 30/40 |
| | | | 705/2 |

FOREIGN PATENT DOCUMENTS

| | | |
|---|---|---|
| CN | 102429679 | 5/2012 |
| CN | 102663416 | 9/2012 |

(Continued)

OTHER PUBLICATIONS

Baoyoubi1989 [online], "Chapter 7 Image Segmentation Technology 3", Sep. 29, 2017, retrieved on Oct. 9, 2021, retrieved from URL<https://www.docin.com/p-2025656846.html>, 37 pages (with English translation).

(Continued)

*Primary Examiner* — Stephen P Coleman
(74) *Attorney, Agent, or Firm* — Fish & Richardson P.C.

(57) ABSTRACT

Methods, devices, systems and apparatus for determining emphysema thresholds for processing a pulmonary medical image are provided. In one aspect, a method includes: determining lung lobe regions in the pulmonary medical image, and, for each of the lung lobe regions, clustering CT values in the lung lobe region to divide the lung lobe region into a first sub region and a second sub region and acquiring a CT value corresponding to an intersection of a first CT value distribution function for the first sub region and a second CT value distribution function for the second sub region in the lung lobe region as an emphysema threshold for the lung lobe region.

17 Claims, 6 Drawing Sheets

(51) Int. Cl.
  *G06K 9/62* (2022.01)
  *G06N 7/00* (2006.01)
  *G06T 5/20* (2006.01)
  *G06T 7/00* (2017.01)

(52) U.S. Cl.
  CPC ............... *G06N 7/005* (2013.01); *G06T 5/20* (2013.01); *G06T 7/0012* (2013.01); *G06T 2207/10081* (2013.01); *G06T 2207/20021* (2013.01); *G06T 2207/30061* (2013.01)

(58) Field of Classification Search
  CPC ......... G06N 20/00; G06T 5/20; G06T 7/0012; G06T 2207/10081; G06T 2207/20021; G06T 2207/30061; G06T 7/11; G06T 7/136; G06T 7/62; G06T 7/70; G06V 10/26; G06V 10/28; G06V 20/653
  USPC ....................................................... 600/529
  See application file for complete search history.

(56) References Cited

FOREIGN PATENT DOCUMENTS

| | | |
|---|---|---|
| CN | 104200465 | 12/2014 |
| CN | 104881872 | 9/2015 |
| CN | 104899926 | 9/2015 |
| CN | 105101878 | 11/2015 |
| CN | 107392910 A | 11/2017 |
| CN | 107507197 | 12/2017 |
| JP | 2007289335 | 11/2007 |

OTHER PUBLICATIONS

Office Action in Chinese Application No. 201811073199.5, dated Jul. 21, 2021, 21 pages (with partial English translation).

Song et al., "Estimating fractional vegetation cover at different heights via Kinect". Journal of Beijing Normal University Natural Science, Oct. 17, 2017, 5 pages (with English abstract).

Wang et al, "Optimal Threshold in CT Quantification of Emphysema", Computed Tomography, Dec. 1, 2021, 28 pages.

Vegas-Sanchez-Ferrero, Gonzalo, et al. "Derivation of a test statistic for emphysema quantification." IEEE, International Symposium on Biomedical Imaging IEEE, 2016:1269-1273.

Vogelmeier, Claus F. et al. "Global strategy for the diagnosis, management, and prevention of chronic obstructive pulmonary disease 2017 Report". The American Thoracic Society. Published with permission from the American Thoracic Society Respirology (2017) 22, 575-601.

Haiying Li, "Quantitative Evaluation of Lung Volume and Emphysema in patients with mild COPD in 256-slice CT" Qinghai University, 2013, 20 pages.

* cited by examiner

IMAGE PROCESSING AND EMPHYSEMA THRESHOLD DETERMINATION

CROSS REFERENCE TO RELATED APPLICATIONS

This application is based upon and claims priority to Chinese Patent Application No. 201811073199.5 filed on Sep. 14, 2018, the entire content of which is incorporated herein by reference.

TECHNICAL FIELD

The present application relates to the field of image processing, and in particular, to a method of determining an emphysema threshold, a method of processing a pulmonary medical image and a computer device.

BACKGROUND

In the medical field, in order to provide intermediate results for the diagnosis of emphysema, pulmonary medical images may be processed via relevant client-side devices to obtain some pulmonary features, such as at least one of parameters including a region where emphysema may be present (hereinafter referred to as a candidate emphysema region), a position parameter and a size of the candidate emphysema region, and an air content of lung. Depending on these pulmonary features, a doctor cannot directly derive the diagnosis result of the disease or the health status of a patient, but these pulmonary features can be used as reference data.

When detecting the pulmonary features, a relevant client-side device needs a user, for example, a clinician or an imaging device operator or the like, to manually input a threshold for determining a candidate emphysema region according to his/her accumulated medical knowledge and experience, then determines the candidate emphysema region in a pulmonary medical image based on the threshold, and processes the candidate emphysema region so that one or more emphysema parameters can be measured.

From the above, the detection of pulmonary features via relevant client-side devices depends on the threshold input by relevant users, and the threshold depends on the users' medical knowledge and experience. Therefore, operations of the relevant client-side devices are highly dependent on the users. When there is a great difference among thresholds that are input by different users, it is likely that the pulmonary features measured via the relevant client-side devices with respect to the same pulmonary medical image are greatly different. Accordingly, the accuracy of detecting the pulmonary features via the relevant client-side devices may be very low.

SUMMARY

The present disclosure provides methods, devices, systems and apparatus for processing a pulmonary medical image, particularly including determining emphysema thresholds.

One aspect of the present disclosure features a method of determining emphysema thresholds for processing a pulmonary medical image, the method including: determining lung lobe regions in the pulmonary medical image; and for each of the lung lobe regions, clustering CT values in the lung lobe region to divide the lung lobe region into a first sub region and a second sub region, and acquiring a CT value corresponding to an intersection of a first CT value distribution function for the first sub region and a second CT value distribution function for the second sub region in the lung lobe region as an emphysema threshold for the lung lobe region.

In some implementations, determining the lung lobe regions in the pulmonary medical image includes: extracting a lung parenchymal region from the pulmonary medical image; dividing the lung parenchymal region into a left lung region and a right lung region; determining lung lobe fissure points in the left lung region and the right lung region; constructing a lung lobe fissure surface from the determined lung lobe fissure points; and determining each of the lung lobe regions in the pulmonary medical image based on the lung lobe fissure surface.

In some examples, determining the lung lobe fissure points in the left lung region and the right lung region includes: performing Gaussian filtering on the left lung region and the right lung region; suppressing at least one of local fissure bright spots, blood vessel wall signal points, fissure points near blood vessel walls, or non-planar and non-curved fissure points in the filtered left lung region and right lung region, to obtain a processed left lung region and right lung region; and extracting the lung lobe fissure points from the processed left lung region and right lung region.

In some implementations, clustering the CT values in the lung lobe region to divide the lung lobe region into the first sub region and the second sub region includes: for each of pixels in the lung lobe region, substituting a CT value of the pixel into a probability density function of a Gaussian Mixture Model to calculate a first probability and a second probability of the pixel, where the first probability represents a probability that the pixel belongs to a predetermined first classification, and the second probability represents a probability that the pixel belongs to a predetermined second classification, and classifying the pixel into a classification indicated by a higher one of the first possibility and the second possibility; determining a region formed by pixels classified into the predetermined first classification as the first sub region of the lung lobe region; and determining a region formed by pixels classified into the predetermined second classification as the second sub region of the lung lobe region.

In some implementations, acquiring the CT value corresponding to the intersection of the first CT value distribution function for the first sub region and the second CT value distribution function for the second sub region in the lung lobe region as the emphysema threshold for the lung lobe region includes: acquiring the first CT value distribution function based on CT values in the first sub region of the lung lobe region and predetermined distribution function values of the CT values; acquiring the second CT value distribution function based on CT values in the second sub region of the lung lobe region and predetermined distribution function values of the CT values; calculating the intersection of the first CT value distribution function and the second CT value distribution function; and determining an abscissa value of the intersection as the emphysema threshold for the lung lobe region.

Both of the first CT value distribution function and the second CT value distribution function can be probability density functions in a Gaussian Mixture Model.

Another aspect of the present disclosure features a method of processing a pulmonary medical image, the method including: determining lung lobe regions in the pulmonary medical image; and for each of the lung lobe regions, acquiring an emphysema threshold for the lung lobe region, where the emphysema threshold is a CT value corresponding to an intersection of a first CT value distribution function for a first sub region of the lung lobe region and a second CT value distribution function for a second sub region of the lung lobe region, the first sub region and the second sub region being obtained by clustering CT values in the lung lobe region, and determining a candidate emphysema region in the lung lobe region according to the emphysema threshold for the lung lobe region.

In some implementations, determining the candidate emphysema region in the lung lobe region according to the emphysema threshold for the lung lobe region includes: determining a part of the lung lobe region having CT values smaller than the emphysema threshold for the lung lobe region as the candidate emphysema region in the lung lobe region.

In some implementations, acquiring the emphysema threshold for the lung lobe region includes: clustering the CT values in the lung lobe region to divide the lung lobe region into the first sub region and the second sub region; and acquiring the CT value corresponding to the intersection of the first CT value distribution function for the first sub region and the second CT value distribution function for the second sub region in the lung lobe region as the emphysema threshold for the lung lobe region.

In some examples, clustering the CT values in the lung lobe region to divide the lung lobe region into the first sub region and the second sub region includes: for each of pixels in the lung lobe region, substituting a CT value of the pixel into a probability density function of a Gaussian Mixture Model to calculate a first probability and a second probability of the pixel, where the first probability represents a probability that the pixel belongs to a predetermined first classification, and the second probability represents a probability that the pixel belongs to a predetermined second classification, and classifying the pixel into a classification indicated by a higher one from the first possibility and the second possibility; determining a region formed by pixels classified into the predetermined first classification as the first sub region of the lung lobe region; and determining a region formed by pixels classified into the predetermined second classification as the second sub region of the lung lobe region.

In some examples, acquiring the CT value corresponding to the intersection of the first CT value distribution function for the first sub region and the second CT value distribution function for the second sub region in the lung lobe region as the emphysema threshold for the lung lobe region includes: acquiring the first CT value distribution function based on CT values in the first sub region of the lung lobe region and predetermined distribution function values of the CT values; acquiring the second CT value distribution function based on CT values in the second sub region of the lung lobe region and predetermined distribution function values of the CT values; calculating the intersection of the first CT value distribution function and the second CT value distribution function; and determining an abscissa value of the intersection as the emphysema threshold for the lung lobe region.

Both of the first CT value distribution function and the second CT value distribution function can be probability density functions in a Gaussian Mixture Model.

In some implementations, the method further includes: optimizing the candidate emphysema region using a pre-trained big data analysis model. The pulmonary medical image can be associated with a region of interest of a subject, and the pre-trained big data analysis model can be trained by samples including a plurality of pulmonary medical images obtained from multiple CT scans of the same region of interest of multiple subjects and corresponding emphysema thresholds for the plurality of pulmonary medical images.

A further aspect of the present disclosure features a computing device for processing a pulmonary medical image, the device including: at least one processor; and at least one non-transitory machine readable storage medium coupled to the at least one processor having machine-executable instructions stored thereon that, when executed by the at least one processor, cause the at least one processor to perform operations including: determining lung lobe regions in the pulmonary medical image; and for each of the lung lobe regions, acquiring an emphysema threshold for the lung lobe region, where the emphysema threshold is a CT value corresponding to an intersection of a first CT value distribution function for a first sub region and a second CT value distribution function for a second sub region in the lung lobe region, and the first sub region and the second sub region are obtained by clustering CT values in the lung lobe region, and determining a candidate emphysema region in the lung lobe region according to the emphysema threshold for the lung lobe region.

In some implementations, determining the candidate emphysema region in the lung lobe region according to the emphysema threshold for the lung lobe region includes: determining a part of the lung lobe region having CT values smaller than the emphysema threshold for the lung lobe region as the candidate emphysema region in the lung lobe region.

In some implementations, acquiring the emphysema threshold for the lung lobe region includes: clustering CT values in the lung lobe region to divide the lung lobe region into the first sub region and the second sub region; and acquiring the CT value corresponding to the intersection of the first CT value distribution function for the first sub region and the second CT value distribution function for the second sub region in the lung lobe region as the emphysema threshold for the lung lobe region.

In some examples, clustering the CT values in the lung lobe region to divide the lung lobe region into the first sub region and the second sub region includes: for each of pixels in the lung lobe region, substituting a CT value of the pixel into a probability density function of a Gaussian Mixture Model to calculate a first probability and a second probability of the pixel, where the first probability represents a probability that the pixel belongs to a predetermined first classification, and the second probability represents a probability that the pixel belongs to a predetermined second classification, and classifying the pixel into a classification indicated by a higher one from the first possibility and the second possibility; determining a region formed by pixels classified into the predetermined first classification as the first sub region of the lung lobe region; and determining a region formed by pixels classified into the predetermined second classification as the second sub region of the lung lobe region.

In some implementations, acquiring the CT value corresponding to the intersection of the first CT value distribution function for the first sub region and the second CT value distribution function for the second sub region in the lung lobe region as the emphysema threshold for the lung lobe region includes: acquiring the first CT value distribution function based on CT values in the first sub region of the lung lobe region and predetermined distribution function values of the CT values; acquiring the second CT value distribution function based on CT values in the second sub region of the lung lobe region and predetermined distribution function values of the CT values; calculating the intersection of the first CT value distribution function and the second CT value distribution function; and determining an abscissa value of the intersection as the emphysema threshold for the lung lobe region.

In some implementations, determining the lung lobe regions in the pulmonary medical image includes: extracting a lung parenchymal region from the pulmonary medical image; dividing the lung parenchymal region into a left lung region and a right lung region; determining lung lobe fissure points in the left lung region and the right lung region; constructing a lung lobe fissure surface from the determined lung lobe fissure points; and determining each of the lung lobe regions in the pulmonary medical image based on the lung lobe fissure surface. Determining the lung lobe fissure points in the left lung region and the right lung region can include: performing Gaussian filtering on the left lung region and the right lung region; suppressing local fissure bright spots, blood vessel wall signal points, fissure points near blood vessel walls, and non-planar and non-curved fissure points in the filtered left lung region and right lung region, to obtain a processed left lung region and right lung region; and extracting the lung lobe fissure points from the processed left lung region and right lung region.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

Figure 1A:
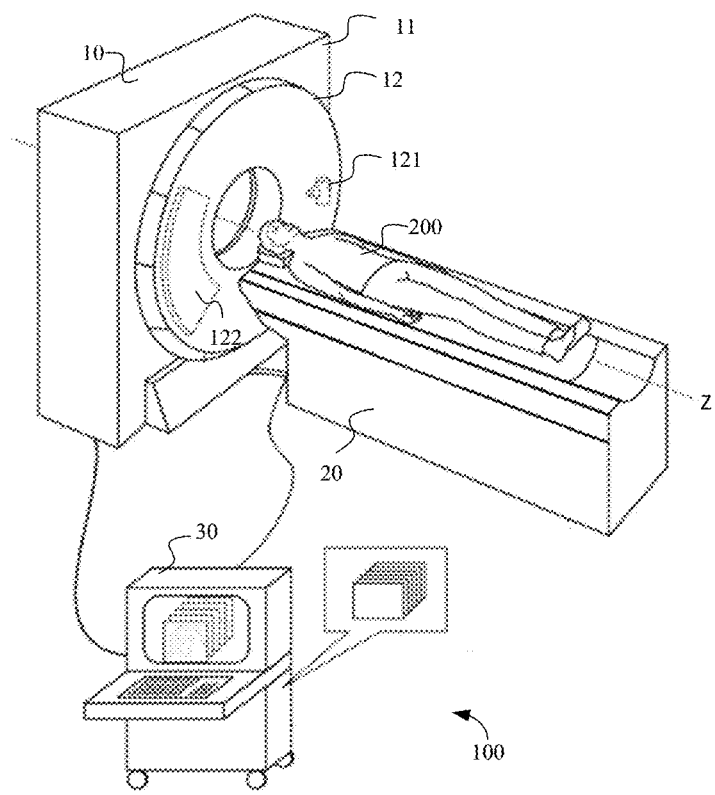
FIGS. 1A and 1B are schematic views showing a structure of a computerized tomography (CT) system according to one or more examples of the present application.

In the medical field, emphysema in lung diseases is a chronic obstructive pulmonary disease (COPD) that seriously threatens human health. Early symptoms are not obvious. With an environmental change, the number of patients can rise up, so early diagnosis and screening of emphysema is essential.

Although the relevant client-side device can detect the pulmonary features through the pulmonary medical image based on the threshold that the relevant user inputs, the threshold depends on the user's medical knowledge and experience. As a result, the operation of the relevant client-side device is highly dependent on the user. When there is a great difference among thresholds input by different users, it is likely that the pulmonary features measured via the relevant clients with respect to the same pulmonary medical image are greatly different.

In view of this, in addition to considering the threshold that the user inputs being limited by the user's medical knowledge and experience, it is also considered that the type of emphysema is not single. Single threshold is suitable only for detecting the diffuse distribution of diseased tissue throughout the entire lung region. In the case where the lesion location is confined to pulmonary segments or some lung tissues (mainly the lung lobe) and other cases, the applicability of setting a single threshold is poor. Implementations of the present application provide a method of determining a threshold suitable for different lung lobe regions, where the threshold is automatically detected by processing a pulmonary medical image.

In some implementations, a method of determining an emphysema threshold includes: after determining lung lobe regions in a pulmonary medical image, with respect to each of the lung lobe regions, CT values in the lung lobe region are clustered to divide the lung lobe region into a first sub region and a second sub region; and a CT value corresponding to an intersection of a first CT value distribution function for the first sub region and a second CT value distribution function for the second sub region in the lung lobe region is acquired as an emphysema threshold for the lung lobe region. Since the emphysema threshold for each of the lung lobe regions is determined by the CT value distribution function thereof, it is not set by a user based on his/her accumulated medical knowledge and experience. As compared with the client-side device that needs the user to input the emphysema threshold to detect the pulmonary features, the solution provided by examples of the present application makes it possible to automatically detect the emphysema threshold, thereby being less dependent on the user.

The emphysema threshold provided by examples of the present application may be used to determine a region in the pulmonary medical image where emphysema may be present. For convenience of description, the region where emphysema may be present hereinafter is called as the candidate emphysema region. The pulmonary medical image is a CT image of lung, which can be generated by a CT system. The CT system for generating the CT image is described below in conjunction with an example.

Figure 1B:
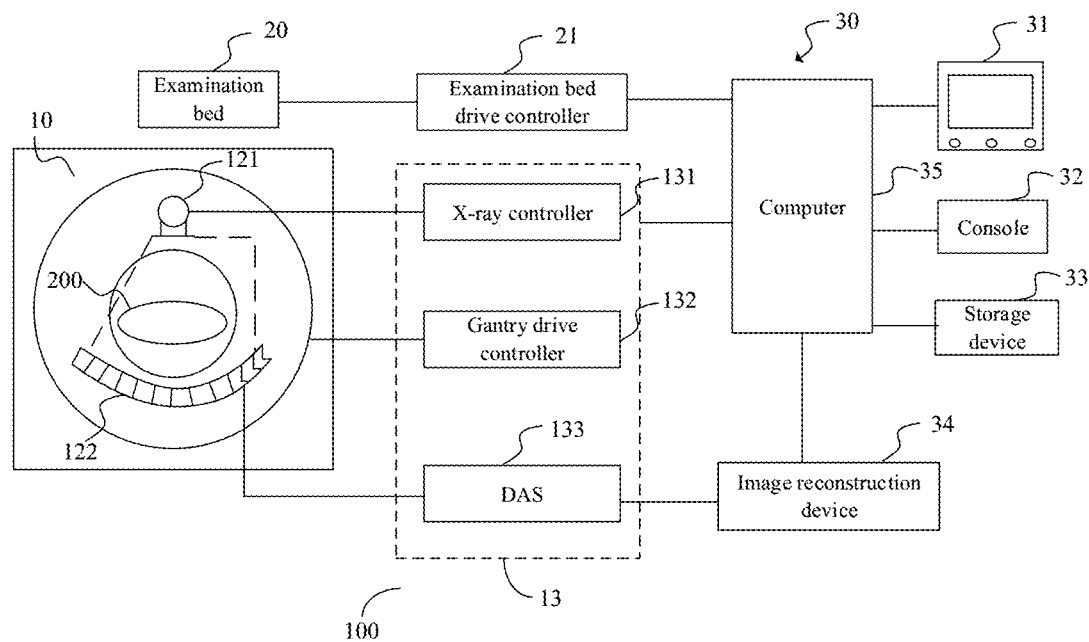

FIG. 1A is a schematic view showing the structure of a CT system 100. FIG. 1B is a block diagram showing the structure of the CT system in FIG. 1A. Viewing in conjunction with FIGS. 1A and 1B, the CT system 100 may include: a gantry 10, an examination bed 20, and a computer system 30.

The gantry 10 is configured to complete scanning in a specific scanning mode, for example, scanning a region of interest of a subject 200 to obtain original data of the region of interest of the subject 200 to be examined, and transmitting the original data to the computer system 30 for image processing to obtain a CT image of the region of interest. In examples of the present application, the region of interest is a lung.

The gantry 10 may include a stationary portion 11 and a rotating portion 12. The stationary portion 11 may be configured to control the inclination angle of the rotating portion 12. As shown in FIG. 1B, the rotating portion 12 may be mounted with a tube 121 for emitting X-rays in a direction perpendicular to a Z-axis direction. An X-ray detector 122 for detecting the intensity of the X-rays may be mounted at a position of the rotating portion 12 opposite to the tube 121. It is noted that the X-ray detector 122 of some CT devices may be located on the stationary portion 11.

The examination bed 20 is configured to carry the subject 200 and is movable in the Z-axis direction to accurately deliver the subject 200 to a predetermined or appropriate position. It is noted here that in some CT systems, the examination bed 20 is not necessary.

The computer system 30 may be mainly configured to implement three functions: first, controlling the gantry 10 and the examination bed 20, for example, after an operator selects appropriate scanning parameters to initiate scanning, to arrange the sequence of various events during a scanning period; second, performing data processing including pre-processing original data and reconstructing an image using the pre-processed data; and third, displaying the reconstructed image on a display.

To achieve the above functions, the computer system 30 may include a control device 13, an image reconstruction device 34, a computer 35, a display 31, a console 32, and a storage device 33.

The control device 13 may be configured to control the gantry 10 to rotate about the Z axis, which causes the tube 121 and the X-ray detector 122 to rotate together with the gantry 10. The control device may be also configured to control the tube 121 to emit X-rays during the rotation. In examples of the present application, the control device 13 may include: an X-ray controller 131 configured to provide energy and timing signals to the tube 121, a gantry drive controller 132 configured to control a rotational speed and a starting position of the rotating portion 12, and a data acquisition system (DAS) 133 configured to acquire an analog signal from the X-ray detector 122, convert the analog signal into a digital signal for subsequent image processing, and output the digital signal as scan data to the image reconstruction device 34 connected therewith.

The image reconstruction device 34 may be configured to perform image reconstruction according to the scan data from the data acquisition system 133 to obtain a reconstructed CT image.

In some scenarios, when the gantry 10 rotates with time, the rotation of the gantry 10 may cause the tube 121 to emit X-rays from different angles to the lung of the subject 200. Accordingly, the data acquisition system 133 acquires the analog signal from the X-ray detector 122, converts the analog signal into the digital signal for subsequent image processing, and outputs the digital signal to the image reconstruction device 34 connected therewith. The image reconstruction device 34 may then reconstruct a series of CT images based on the digital signal. This series of CT images may be referred to as pulmonary medical image sequence.

The computer 35 may be configured to convert commands and parameters input by an operator through the console 32 into control signals or information and transmit the control signals or information to the control device 13 and/or an examination bed drive controller 21. The computer 35 may also receive and store the CT image reconstructed by the image reconstruction device 34.

The display 31 is configured to display the reconstructed image and related data.

The console 32 is configured to receive the commands and scan parameters input by the operator.

The storage device 33 is configured to store the reconstructed CT image. In some scenarios, the computer 35 may also transmit the CT image in a DICOM format or other formats to a server that stores CT images for sharing the CT images with other computer terminals. Digital Imaging and Communications in Medicine (DICOM) mentioned here is an international standard for the communication and management of medical imaging information and related data (ISO 12052).

In some examples, the method of determining the emphysema threshold according to the present application may be applied to the computer system 30. Specifically, after the image reconstruction device 34 reconstructs a pulmonary CT image, the image reconstruction device 34 or the computer 35 determines lung lobe regions of the pulmonary CT image, which serves as the pulmonary medical image; with respect to each of the lung lobe regions, the image reconstruction device 34 or the computer 35 clusters CT values in the lung lobe region to divide the lung lobe region into a first sub region and a second sub region; and the image reconstruction device 34 or the computer 35 acquires a CT value corresponding to an intersection of a first CT value distribution function for the first sub region and a second CT value distribution function for the second sub region in the lung lobe region as an emphysema threshold for the lung lobe region. In other examples, the method of determining the emphysema threshold may be applied to a computer device external to (or separate from) the computer system 30. The computer device may acquire a pulmonary CT image from the computer system 30 or an image server in real time, or pre-store the pulmonary CT image, and then determine an emphysema threshold. An image processing procedure according to the examples of the present application will be described below in detail with reference to the accompanying drawings.

Figure 2A:
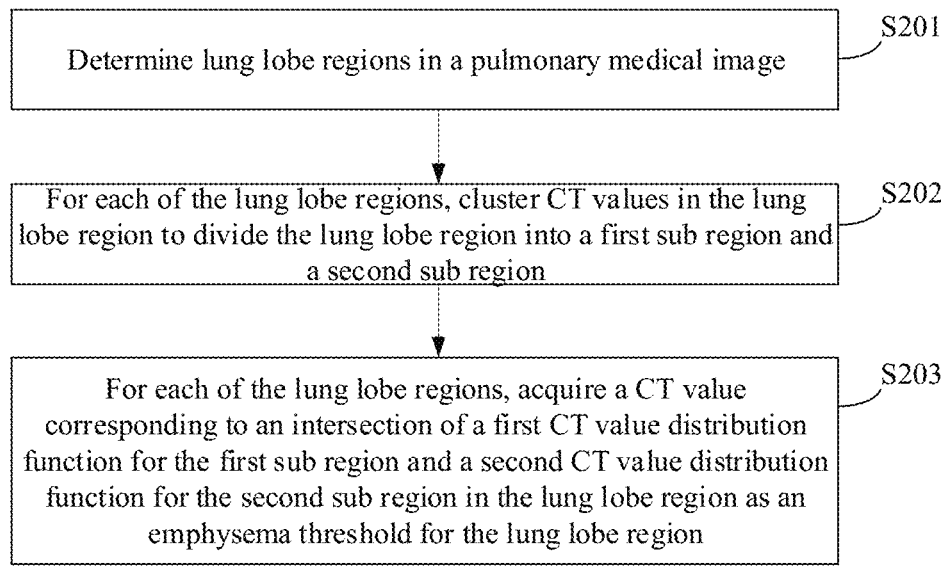
FIG. 2A is a flowchart showing a method of determining an emphysema threshold according to one or more examples of the present application.

FIG. 2A is a flowchart of a process showing a method of determining an emphysema threshold according to one or more examples of the present application, which may be performed by a computer device. The process can include steps S201 to S203.

In step S201, lung lobe regions in a pulmonary medical image are determined.

In step S202, for each of the lung lobe regions, CT values in the lung lobe region are clustered to divide the lung lobe region into a first sub region and a second sub region.

In step S203, for each of the lung lobe regions, a CT value corresponding to an intersection of a first CT value distribution function for the first sub region and a second CT value distribution function for the second sub region in the lung lobe region is acquired as an emphysema threshold for the lung lobe region.

The computer device according to the examples of the present application, as described above, may either be the image reconstruction device 34 or the computer 35 in the computer system 30, or be a computer device having image processing capabilities and being external to the computer system 30.

In some examples, after a pulmonary CT image is reconstructed by the image reconstruction device 34, received from the image reconstruction device 34, or acquired from the image server, normalization pre-processing may be performed on the pulmonary CT image, and then the pre-processed pulmonary CT image is used as a pulmonary medical image. Subsequently, the pulmonary medical image is divided using the relevant lung division technique to obtain individual lung lobe regions.

Figure 2B:
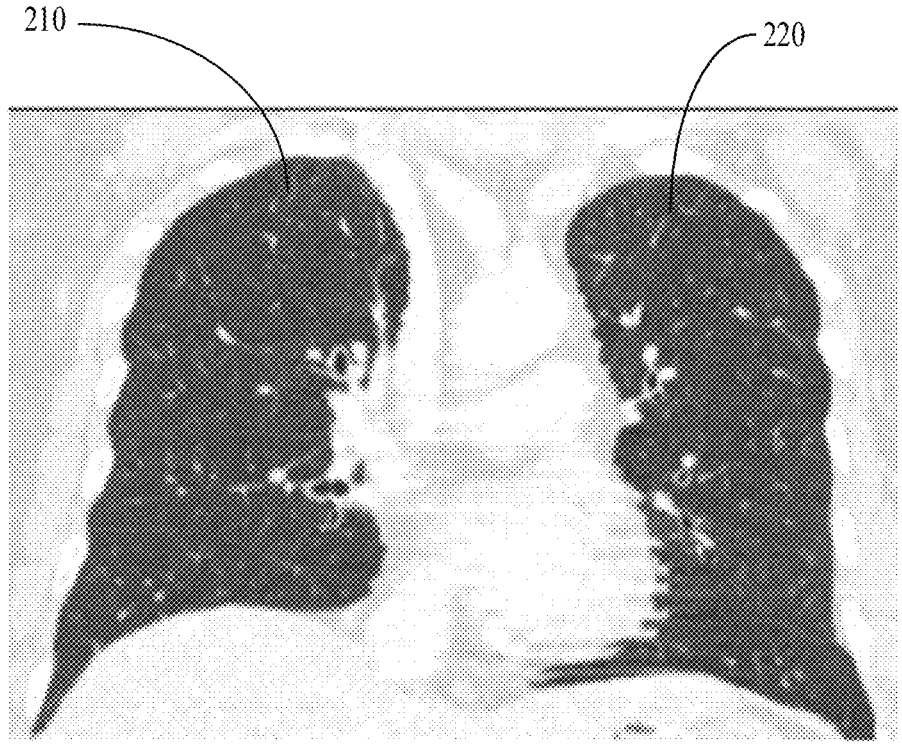
FIG. 2B is a schematic view showing a lung parenchymal region according to one or more examples of the present application.
Figure 2C:
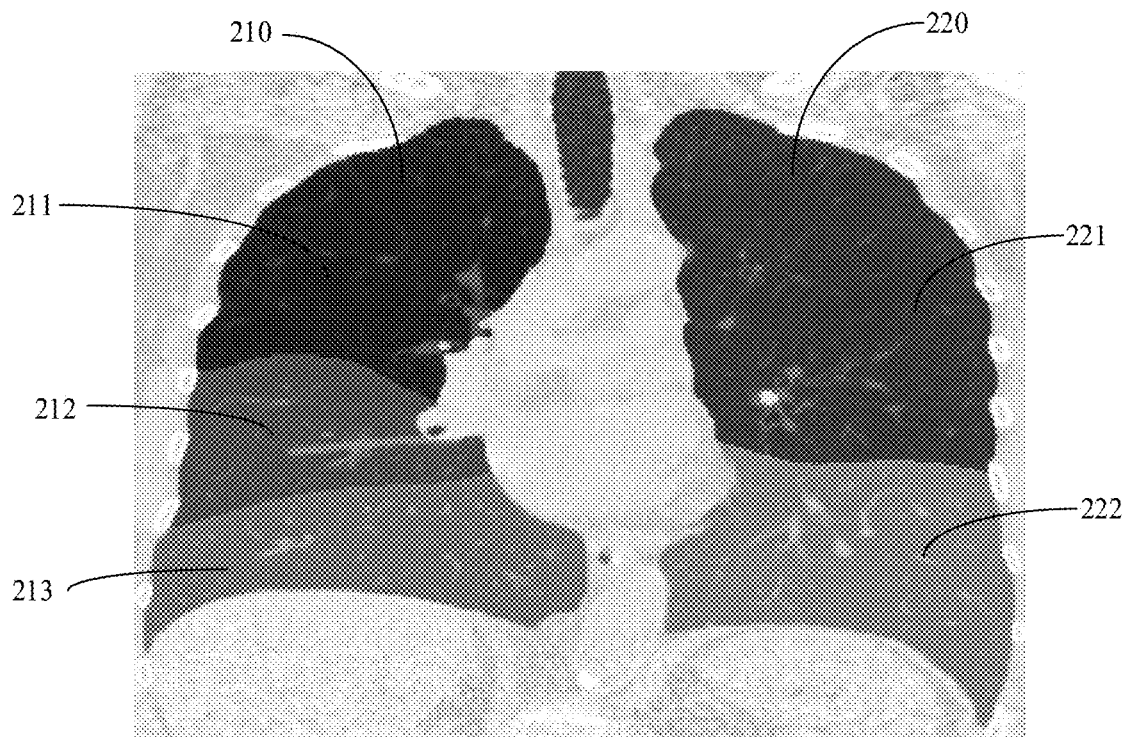
FIG. 2C is a schematic view showing each lung lobe region according to one or more examples of the present application.

It is noted that when the CT system generates a pulmonary CT image, the chest is directly photographed. Therefore, the reconstructed CT image includes images of tissues other than lung. The lung parenchymal region needs to be extracted from the reconstructed CT image, and the boundary between a left lung region and a right lung region is required to be determined. Division of lung lobes may be performed within the left lung region and the right lung region after determining the two regions through the division of the pulmonary medical image. The extracted lung parenchymal region is as shown in FIGS. 2B-2C. The left lung region 220 includes two lung lobes 221 and 222, and the right lung region 210 includes three lung lobes 211, 212 and 213.

In some examples, when determining the lung lobe regions, the two lung lobes 221 and 222 in the left lung region 220 may be determined as one lung lobe region, and the three lung lobes 211, 212 and 213 in the right lung region 210 may be determined as the other lung lobe region, or each of lung lobes 221, 222, 211, 212 and 213 may be regarded as one lung lobe region so that a total of five lung lobe regions are determined. The number of the lung lobe regions may be determined specifically according to actual application requirements, and examples of the present application will not make any limitation in this regard.

In some examples, the lung lobe regions in the pulmonary medical image may be determined by the following operations including: extracting a lung parenchymal region from the pulmonary medical image; dividing the lung parenchymal region into a left lung region and a right lung region; determining lung lobe fissure points in the left lung region and the right lung region; constructing a lung lobe fissure surface from the determined lung lobe fissure points; and determining each of the lung lobe regions in the pulmonary medical image based on the lung lobe fissure surface.

The lung parenchymal region may be extracted based on the characteristics of lung, such as morphology and grey scale, or using an automatic threshold algorithm or other related methods in the art, which will not be described herein.

In some examples, to avoid the influence of trachea on the division of the lung lobes, tracheal tissues may be removed from the lung parenchymal region, and then the lung parenchymal region in which the tracheal tissues are removed is divided into a left lung region and a right lung region. The tracheal tissues can be removed by wavefront detection and low threshold region growing algorithm or other suitable methods, which will not be described herein.

In addition, considering that there may be a plurality of local fissure bright spots, blood vessel wall signal points, fissure points near blood vessel walls, and non-planar and non-curved fissure points in the CT image, and the presence thereof may cause interference to the extraction of the lung lobe fissure points. In some examples, to reduce the influence of the interference, these points, including local fissure bright spots, blood vessel wall signal points, fissure points near blood vessel walls, and non-planar and non-curved fissure points, may be suppressed when extracting the lung lobe fissure points, as discussed with details below. The lung lobe fissure surface is then constructed from the determined lung lobe fissure points. The Hessian matrix may be used to determine the lung lobe fissure points, and the lung lobe regions can then be determined based on the lung lobe fissure points. The lung lobe fissure points can be also determined by Walsh transformation or other methods. For illustration purposes only, the following is a brief description of a method of determining lung lobe fissure points using the Hessian matrix.

First, Gaussian filtering is performed on the left lung region and the right lung region. After the Gaussian filtering, a Hessian matrix is constructed for each pixel in the left lung region and the right lung region, and three eigenvalues of the Hessian matrix are obtained through QR decomposition, which are respectively recorded as a first eigenvalue $\lambda 1$, a second eigenvalue $\lambda 2$, and a third eigenvalue $\lambda 3$, where $|\lambda 1| \leq |\lambda 2| \leq |\lambda 3|$.

The lung lobe fissure points are extracted according to formula (1):

$$F = \Gamma F_{plane} F_{wall} F_{vessels} \tag{1}$$

The pixels with corresponding F values greater than a predetermined threshold are extracted as the lung lobe fissure points.

$\Gamma$ is used to suppress local fissure bright spots, that is, to suppress the points where the third eigenvalue $\lambda 3$ is positive. $\Gamma$ can be determined according to formula (2):

$$\Gamma = \begin{cases} 1, & \lambda_3 < 0 \\ 0, & \lambda_3 \geq 0 \end{cases}. \tag{2}$$

$F_{plane}$ in formula (1) is used to suppress non-planar and non-curved fissure points. As the value of $F_{plane}$ approaches 1, the point is likely to be on a plane or curve; as the value of $F_{plane}$ approaches 0, the point is far away from the plane or curve. The points where the $F_{plane}$ approaches 0 are removed. The $F_{plane}$ can be determined according to formula (3):

$$F_{plane} = \exp\left(-\frac{\left(\frac{|\lambda_2|}{|\lambda_3|}\right)^2}{2p^2}\right), \tag{3}$$

where p is a preset value and may be an empirical value set based on $\lambda 2$ and $\lambda 3$. In an example, p=0.5.

$F_{wall}$ in formula (1) is used to suppress blood vessel wall signal points. The blood vessel wall signal point may have a relatively larger second eigenvalue than the fissure points. The $F_{wall}$ can be calculated according to formula (4):

$$F_{wall} = \exp\left(-\frac{(\lambda_1^2 + \lambda_2^2)}{2w^2}\right), \tag{4}$$

where w is a preset value and may be an empirical value set based on $\lambda 1$ and $\lambda 2$. In an example, w=3.

$F_{vessels}$ in formula (1) is used to suppress fissure points near blood vessel walls. In an example, $F_{vessels}$ is used to suppress capillaries. The $F_{vessels}$ can be calculated according to formula (5):

$$F_{vessels} = \exp\left(1 - \frac{DT\{vessels\}^2}{2v^2}\right), \quad (5)$$

where $DT\{vessels\}^2$ represents the distance transformation of blood vessels computed with watershed algorithm. Distance transformation is very sensitive to small blood vessels like capillaries. Since the small blood vessels may approach or even cross the boundary between lung lobes, they may cause errors in division of lung lobe regions. Based on this, it is necessary to suppress the fissure points near the blood vessel walls. v represents an eigen distance. In one example, v is set to be 5 mm.

Pixels with corresponding F values smaller than the predetermined threshold are removed, such that the pixels with the corresponding F values smaller than the predetermined threshold do not participate in fitting of the lung lobe fissure surface. In the method of determining the lung lobe fissure points as described above, noises in the pulmonary medical image may be filtered through Gaussian filtering, and then the lung lobe fissure points are extracted from the pixels in the left lung region and the right lung region. Since the local fissure bright spots, the blood vessel wall signal points, the fissure points near the blood vessel walls, and the non-planar and non-curved fissure points are suppressed during the extraction of the lung lobe fissure points, the lung lobe fissure points obtained thereby are relatively accurate.

In some examples, after the lung lobe fissure points are extracted, surface fitting may be performed on the extracted lung lobe fissure points through a surface fitting algorithm to obtain a lung lobe fissure surface, that is, the lung lobe fissure surface can be constructed from the lung lobe fissure points. The lung parenchymal region can be divided by the fitted lung lobe fissure surfaces into different lung lobe regions. The divided lung lobe regions are as shown in FIG. 2C, including a total of five lung lobe regions, two lung lobes 221 and 222 in the left lung region 220 and three lung lobes 211, 212 and 213 in the right lung region 210.

In other examples, lung lobe regions may be predetermined by the above manner of determining the lung lobe regions, and then the predetermined lung lobe regions may be directly retrieved when the emphysema threshold needs to be determined.

After the lung lobe regions are determined, there may be an emphysema lesion region and a healthy tissue region in different lung lobe regions. The emphysema lesion region contains a lot of air, and the CT value of air is usually lower than that of non-air tissue, thus the CT value of the emphysema lesion region can be lower than that of the healthy tissue region. In view of the difference in CT values between the emphysema lesion region and the healthy tissue region, the lung lobe region can be divided into two sub regions by clustering the CT values, one of which represents the healthy tissue region, and the other of which represents a region where an emphysema lesion is potentially contained.

After the clustering, the two sub regions of each of the lung lobe regions are obtained and an overlapping region is likely to be present in CT value distributions for the two sub regions. However, the presence of the overlapping region will affect the accuracy of emphysema location, and it is difficult to clearly divide candidate emphysema regions. In the present application, the CT value corresponding to the intersection of the CT value distribution functions for the two sub regions is determined as the emphysema threshold for the lung lobe region, which can be used to better distinguish the candidate emphysema region.

The CT value mentioned here may be a value of each tissue in a CT image, the value corresponding to an X-ray attenuation coefficient. Both of matrix images and matrix numerals are representatives of the CT value, and the CT value is derived from the conversion of linear attenuation coefficients (µ values) of human tissues and organs. The CT value of the voxel may be obtained based on linear attenuation coefficients of water, of air, and of the voxel. In addition, the emphysema threshold may be either the CT value (hereinafter also referred to as $CT_{intersection}$) at the intersection of the CT value distribution functions for the two sub regions of the lung lobe region, or an adjusted value (hereinafter also referred to as $CT_{adjusted}$) of the $CT_{intersection}$. The adjustment range of $CT_{adjusted}$ relative to $CT_{intersection}$ may be decided according to actual application requirements. For example, an adjustment of 1% may be made, that is, $CT_{adjusted} = (1+1\%) * CT_{intersection}$.

Figure 3:
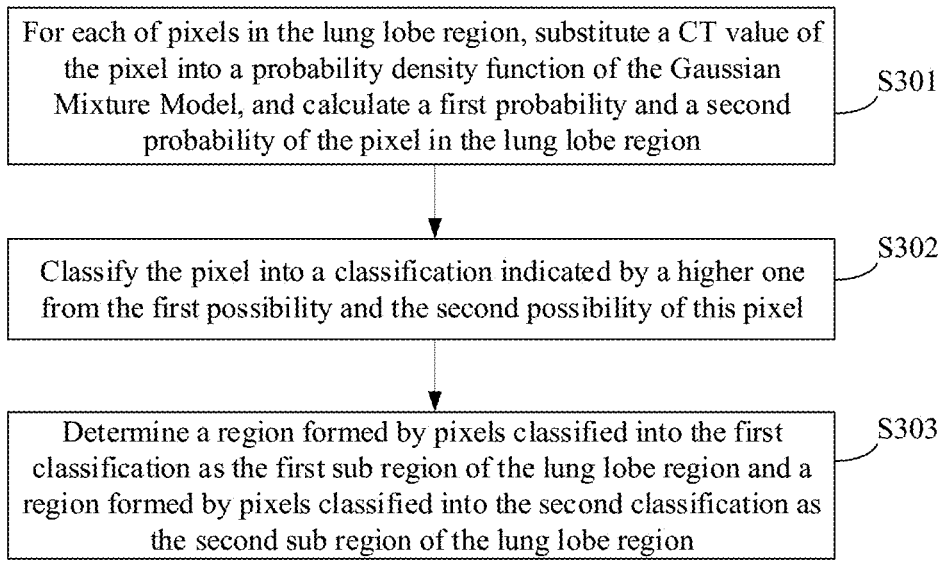
FIG. 3 is a flowchart of a process showing a method of determining an emphysema threshold according to one or more examples of the present application.

When clustering CT values, various clustering methods such as K-means, fuzzy C-means, and hierarchical clustering may be adopted. In an example, for each of the lung lobe regions, respective pixels in the lung lobe region are substituted into a clustering formula, thereby dividing all pixels in the lung lobe region into two classifications. The Gaussian Mixture Model (GMM) algorithm is taken as an example to introduce the process of dividing each of the lung lobe regions. As illustrated in FIG. 3, a process of a method of dividing a lung lobe region into a first sub region and a second sub region can include steps S301-S303.

In step S301, for each of pixels in the lung lobe region, a CT value of the pixel is substituted into a probability density function of the Gaussian Mixture Model, and a first probability and a second probability of the pixel in the lung lobe region are calculated. The first probability represents a probability that the pixel belongs to a predetermined first classification, and the second probability represents a probability that the pixel belongs to a predetermined second classification.

In step S302, for each of the pixels in the lung lobe region, the pixel is classified into a classification indicated by a higher one from the first possibility and the second possibility of this pixel. For example, when the first probability of the pixel is greater than the second probability of the pixel, the pixel is classified into the first classification; when the first probability of this pixel is less than the second probability of the pixel, the pixel is classified into the second classification.

In step S303, a region formed by pixels classified into the first classification is determined as the first sub region of the lung lobe region, and a region formed by pixels classified into the second classification is determined as the second sub region of the lung lobe region.

In some examples, the lung lobe region may be either one of the left lung lobe region and the right lung lobe region, or be any one of the five lung lobe regions. Correspondingly, in step S301, each of the left lung lobe region and the right lung lobe region, or each of the five lung lobe regions may be sequentially selected, and the CT value of each pixel in the selected lung lobe region is substituted into the following formulas (6)-(7):

$$P(y \mid \theta) = \sum_{k=1}^{K} \alpha_k \phi(y \mid \theta_k); \quad (6)$$

$$\theta = f(\mu, \sigma^2)$$

$$\phi(y \mid \theta) = \frac{1}{\sqrt{2\pi}\sigma} e^{-\frac{(y-\mu)^2}{2\sigma^2}}; \quad (7)$$

$$\alpha_k = P(z = k \mid \theta),$$

where, $\mu$ and $\sigma^2$ respectively represent the mean and variance of a sample, $\alpha_k$ represents a probability that a classification k in a sample set is selected, and z=k represents that the sample belongs to the classification k.

In addition, the CT value is not an absolutely constant value. It is related not only to internal factors such as breathing and blood flow of a human body, but also to external factors such as the voltage of X-ray tube, CT apparatus, and room temperature, and may be corrected frequently.

Figure 4A:
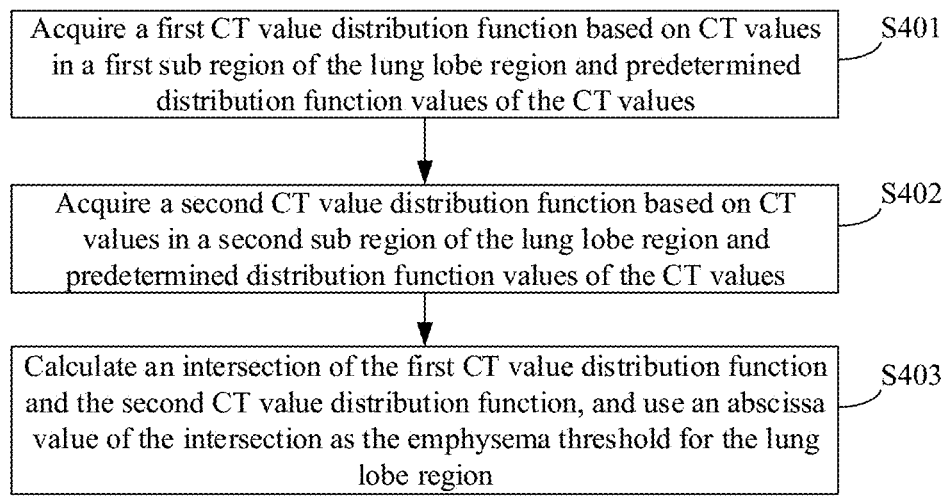
FIG. 4A is a flowchart of a process showing a method of determining an emphysema threshold according to one or more examples of the present application.

After dividing each of the lung lobe regions into two sub regions, based on the feature that CT values of the two sub regions in each of the lung lobe regions are distributed in a different way, a CT value corresponding to an intersection of CT value distribution functions may be directly calculated and determined as the emphysema threshold for the lung lobe region. A method of calculating an intersection of CT value distribution functions will be introduced below. As shown in FIG. 4A, a process of a method of determining an emphysema threshold for a lung lobe region may include steps S401-S403.

In step S401, a first CT value distribution function is acquired based on CT values in a first sub region of the lung lobe region and predetermined distribution function values of the CT values.

In some examples, the first CT value distribution function is acquired with a nonlinear data-fitting algorithm based on CT values in the first sub region of the lung lobe region and predetermined distribution function values of the CT values. In some example, the nonlinear data-fitting algorithm includes, but not limited to, a Nonlinear least Squares Fitting Algorithm.

In step S402, a second CT value distribution function is acquired based on CT values in a second sub region of the lung lobe region and predetermined distribution function values of the CT values.

In some examples, the second CT value distribution function is acquired with the nonlinear data-fitting algorithm based on CT values in the second sub region of the lung lobe region and predetermined distribution function values of the CT values.

In step S403, an intersection of the first CT value distribution function and the second CT value distribution function is calculated, and an abscissa value of the intersection is used as the emphysema threshold for the lung lobe region.

In some examples, the abscissa value of the intersection is used as the emphysema threshold for the lung lobe region. In some examples, the abscissa value of the intersection may be adjusted to a certain extent, and the adjusted abscissa value is then used as the emphysema threshold for the lung lobe region. The examples of the present application will not make any limitation in this regard.

Further, a predetermined CT value distribution function may have CT values of pixels as the abscissa and the number of pixels with the same CT value as the ordinate. Alternatively, the predetermined CT value distribution function may also have the CT values of the pixels as the abscissa and the dependent variable of a function in which CT value is an independent variable as the ordinate. For example, the CT value distribution function may be a probability density function in Gaussian Mixture Model, where a CT value distribution function value corresponds to a probability density function value in the Gaussian Mixture Model. Here, the left lung lobe region and the right lung lobe region are taken as an example to illustrate the emphysema threshold for each of the lung lobe regions in conjunction with FIGS. 4B and 4C.

Figure 4B:
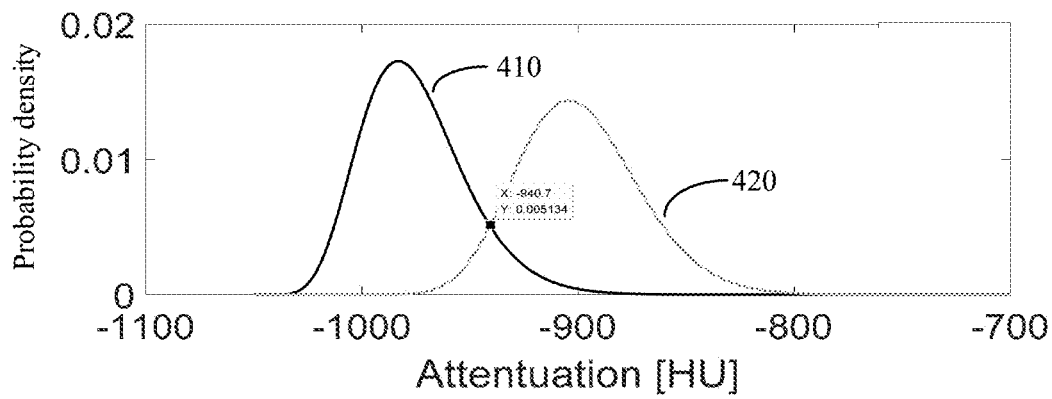
FIG. 4B is a schematic view showing a CT value distribution function for two sub regions in a lung lobe region according to one or more examples of the present application.

FIG. 4B is a graph showing an example of the CT value distribution functions for the two sub regions of the left lung lobe region. The curve 410 on the left is a graph showing the CT value distribution function for a sub region where emphysema may be present, and the curve 420 on the right is a graph showing the CT value distribution function for a sub region indicating a healthy tissue region.

The intersection of the two curves 410 and 420 indicates the emphysema threshold for the left lung lobe region. As shown in FIG. 4B, the emphysema threshold for the left lung lobe region is approximately −940.7 Hounsfield units.

Figure 4C:
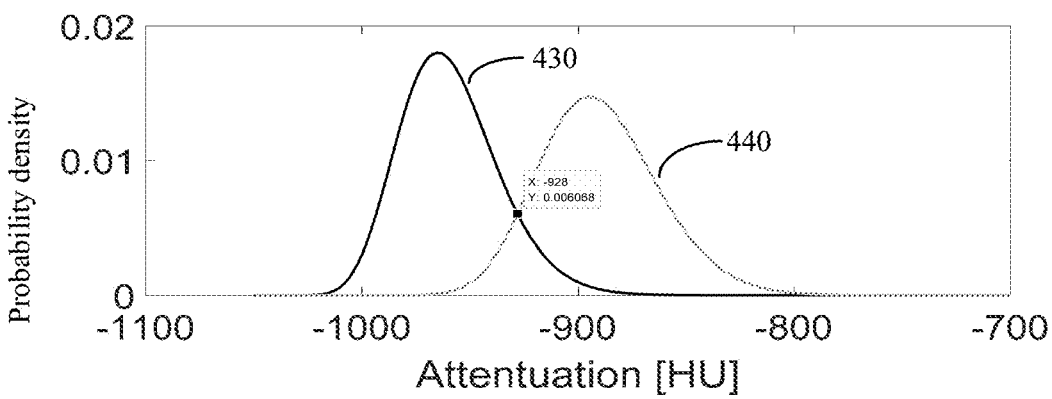
FIG. 4C is a schematic view showing a CT value distribution function for two sub regions in a lung lobe region according to one or more examples of the present application.

FIG. 4C is a graph showing the CT value distribution functions for the two sub regions of the right lung lobe region. The curve on the left 430 is a graph showing the CT value distribution function for a sub region where emphysema may be present, and the curve 440 on the right is a graph showing the CT value distribution function for a sub region indicating a healthy tissue region.

The intersection of the two curves 430 and 440 indicates the emphysema threshold for the right lung lobe region. As shown in FIG. 4C, the emphysema threshold for the right lung lobe region is approximately −928 Hounsfield units.

After the emphysema threshold for each of the lung lobe regions is determined, the determined emphysema threshold for each of the lung lobe regions may be applied to a scenario in which a candidate emphysema region needs to be determined.

In a practical application, the emphysema threshold for each of the lung lobe regions may be stored for subsequent use in determining the candidate emphysema region. It is also feasible, after determining the lung lobe regions, to immediately determine the candidate emphysema region in each of the lung lobe regions according to the emphysema threshold for each of the lung lobe regions. An image processing method of determining a candidate emphysema region will be introduced below.

Figure 5:
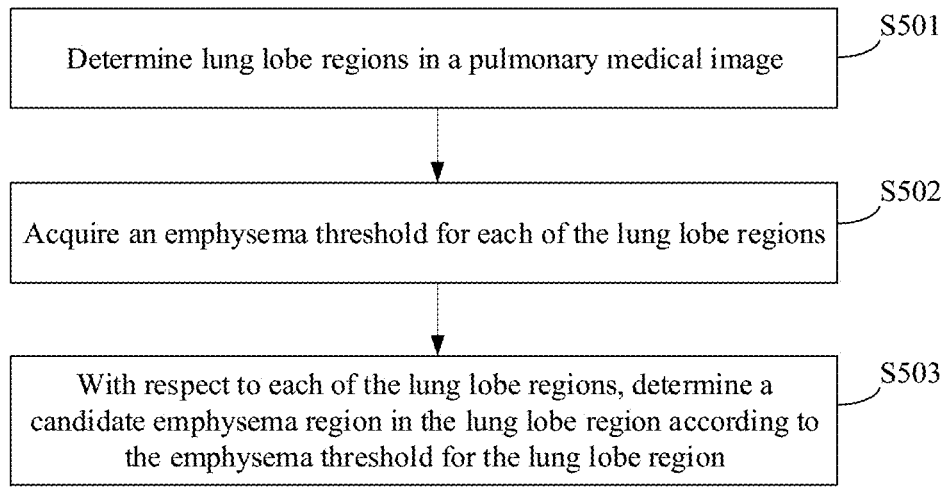
FIG. 5 is a flowchart of a process showing a method of processing a pulmonary medical image according to one or more examples of the present application.

FIG. 5 is a flowchart of a process showing a method of processing a pulmonary medical image according to one or more examples of the present application. The process may be performed by a computer device and can include steps S501 to S503.

In step S501, lung lobe regions in a pulmonary medical image are determined.

In step S502, an emphysema threshold for each of the lung lobe regions is acquired. The emphysema threshold for a lung lobe region is a CT value corresponding to an intersection of CT value distribution functions for two sub regions in the lung lobe region. The two sub regions of the lung lobe region are obtained by clustering of CT values in the lung lobe region.

In step S503, for each of the lung lobe regions, a candidate emphysema region in the lung lobe region is determined according to the emphysema threshold for the lung lobe region.

For some technical features in examples of the present application, such as the method of determining the lung lobe regions, reference may be made to the examples involving the method of determining the emphysema threshold, which will not be described here repeatedly.

When the emphysema threshold for each of the lung lobe regions is acquired, the emphysema threshold predetermined by the above-described method of determining the emphysema threshold may be directly retrieved. It is also feasible to determine in real time using the above-described method of determining the emphysema threshold. Their difference lies in that it is unnecessary for the former method to re-determine the lung lobe regions in a pulmonary medical image when acquiring the emphysema threshold for each of the lung lobe regions.

After the emphysema threshold for each of the lung lobe regions is acquired, the lung lobe region may be divided, for example, into a healthy tissue region and a region where emphysema may be present, according to the emphysema threshold, to obtain a candidate emphysema region. In the actual division, considering such characteristic that CT values of the emphysema lesion region are lower than those of the healthy tissue region, a part of a lung lobe region having CT values smaller than the emphysema threshold for the lung lobe region may be divided as a candidate emphysema region, and the remaining region of the lung lobe region is divided as a healthy tissue region. In other examples, a part of a lung lobe region may also be divided as a candidate emphysema region, a difference between each of CT values in the part of the lung lobe region and the emphysema threshold for the lung lobe region being within a certain range, and the specific division method will not be described herein.

Further, it is considered that if multiple CT scans are performed on the same region of interest of the subject, CT values obtained by the multiple CT scans in the same scenario may be different due to devices and operators. Since the CT values obtained by multiple CT scans in the same scenario are different, the candidate emphysema region of the subject determined by each CT scan may be different, and thus the determined candidate emphysema region is not particularly accurate. Therefore, to obtain a candidate emphysema region in a better and more accurate manner, the emphysema threshold for each lung lobe region in a large number of history pulmonary medical images obtained through a large number of previous CT scans may be calculated according to the method of determining the emphysema threshold provided in the examples of the present application. The large number of previous CT scans may be performed on the same region of interest of multiple subjects. Then, after sorting the emphysema thresholds from the large number of history pulmonary medical images, the large number of history pulmonary medical images and corresponding emphysema thresholds are input as samples into a big data analysis model, e.g., a model corresponding to methods such as regression and cross validation, to train a candidate emphysema region optimum model. In some examples, after determining a current candidate emphysema region in the pulmonary medical image, the determined candidate emphysema region may be optimized using a pre-trained big data analysis model, that is, the above-described candidate emphysema region optimum model. In this way, the optimized candidate emphysema region can be more accurate and can be independent of devices and operators.

After determining the candidate emphysema region, each candidate emphysema region may be marked on the pulmonary medical image. For example, the candidate emphysema region may be highlighted in the pulmonary medical image or marked with a color value or a grayscale value different from that for the healthy tissue region.

In the examples of the present application, at least one of the following emphysema parameters may be calculated according to the candidate emphysema regions in the pulmonary medial image: position coordinates of each candidate emphysema region, a volume of each candidate emphysema region, a surface area of each candidate emphysema region, and an air content of lung.

In the examples of the present application, at least one of the following lung parameters may be calculated according to the pulmonary medical image: a pulmonary CT mean, a lung volume, a lung surface area, a pulmonary tissue volume, a pulmonary tissue weight, a pulmonary tissue density, a left lung volume, a right lung volume, and a pulmonary trachea volume.

The volume V of the candidate emphysema region can be calculated according to formula (8) as follows:

$$V = \frac{PixelArea * PixelNum * SliceThick}{1000}, \tag{8}$$

where PixelArea represents the area of a single pixel, PixelNum represents the number of pixels in the candidate emphysema region, and SliceThick represents the slice thickness of the pulmonary medical image.

The surface area A of the candidate emphysema region can be calculated according to formula (9) as follows:

$$A = \frac{EdgePixel * PixelNum * SliceThick}{100}, \tag{9}$$

where EdgePixel represents a side length of a single pixel, PixelNum represents the number of pixels in the candidate emphysema region, and SliceThick represents the slice thickness of the pulmonary medical image.

The air content C of lung can be calculated according to formula (10) as follows:

$$C = \frac{lungSum}{1000} * pixelVolume, \tag{10}$$

where lungSum represents the accumulated value of the air content of each pixel, and pixelVolume represents the volume of a single pixel.

The pulmonary tissue volume Vpt can be calculated according to formula (11) as follows:

$$Vpt = (lungNumA + lungNumB) * pixelVolume \tag{11},$$

where lungNumA represents the number of air containing pixels, lungNumB represents the number of non-air containing pixels, and pixelVolume represents the volume of a single pixel.

In the scenario where the determined emphysema threshold is applied to the determination of a candidate emphysema region, based on the method of processing a pulmonary medical image provided by examples of the present application, different users can determine an identical candidate emphysema region with respect to the same pulmonary medical image, and then the same emphysema parameters or other lung parameters are detected to improve the accuracy of parameter detection.

Further, it is noted that the candidate emphysema region, emphysema parameters or lung parameters obtained by examples of the present application are used only as an intermediate result of emphysema diagnosis, but cannot take the place of doctors for diagnosis of emphysema. The doctor needs to combine other information for comprehensive diagnosis, and the information on which the comprehensive diagnosis is based is difficult to be predicted, which depends on the subject and the doctor.

Corresponding to the example of the method of determining an emphysema threshold and the method of processing a pulmonary medical image in the present application, implementations of the present application also provide an example of an apparatus for determining an emphysema threshold and an apparatus for processing a pulmonary medical image. The apparatus for determining the emphysema threshold and the apparatus for processing a pulmonary medical image may be applied to various computer devices such as personal computers, laptop computers, cellular phones, camera phones, smart phones, tablet computers, smart interactive tablets, smart home devices, or any combination thereof.

Figure 6:
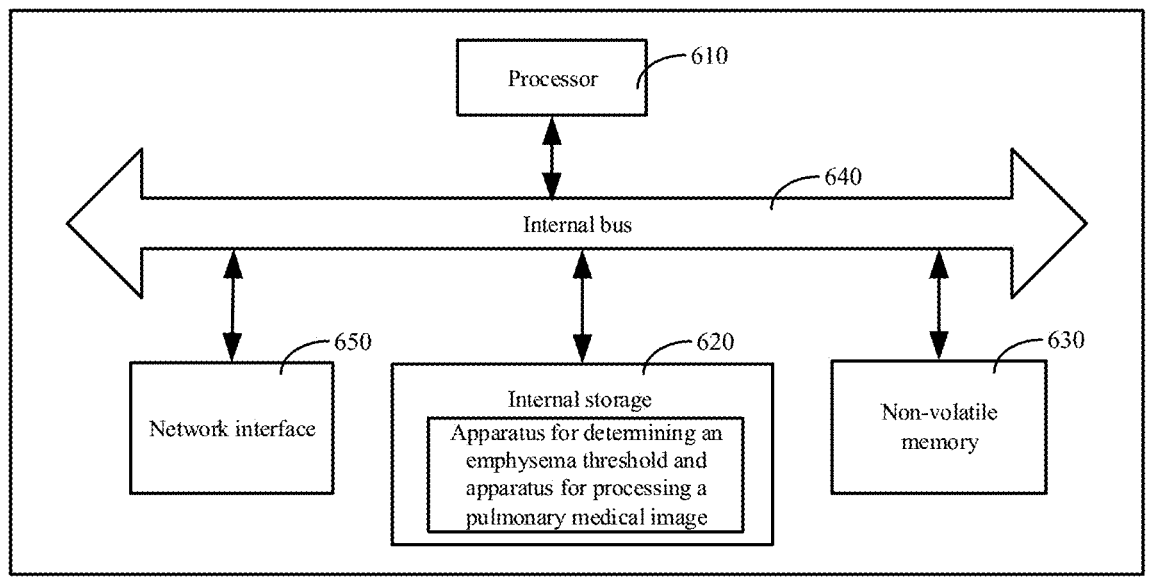
FIG. 6 is a schematic view showing a hardware structure of a computer device according to one or more examples of the present application.

FIG. 6 is a schematic view showing the hardware structure of a computer device applied by the apparatus for determining the emphysema threshold and the apparatus for processing a pulmonary medical image according to one or more examples of the present application. The computer device may include a processor 610, an internal storage 620, and a non-volatile memory 630. The internal storage 620 and the non-volatile memory 630 are machine readable storage media. The processor 610 and the machine readable storage media 620, 630 may be coupled to each other via an internal bus 640. In other possible implementations, the computer device may also include a network interface 650 to enable communication with other devices or components. In addition to the processor 610, the internal storage 620, the network interface 650, and the non-volatile memory 630 shown in FIG. 6, the computer device may further include other hardware according to actual functional requirements, which are not shown in FIG. 6.

In some examples, the machine readable storage media 620, 630 may include a ROM (Read-Only Memory), a volatile memory, a non-volatile memory, a flash memory, a storage drive such as a hard disk drive, a solid state drive, any type of storage disks such as a compact disc and a DVD, or similar storage media, or a combination thereof.

Figure 7:
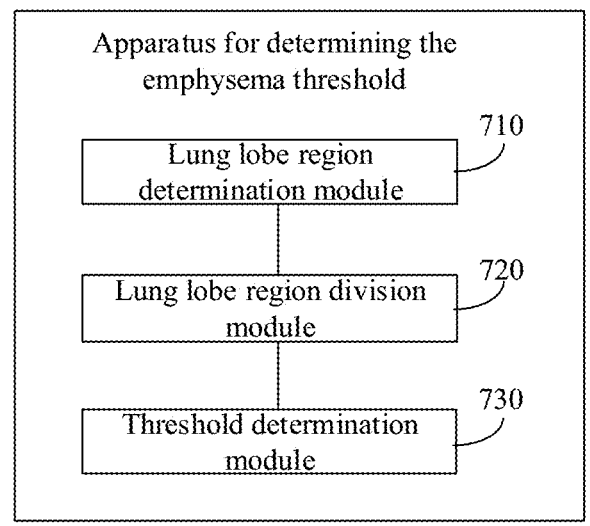
FIG. 7 is a block diagram showing an apparatus for determining an emphysema threshold according to one or more examples of the present application.

Further, machine executable instructions corresponding to the apparatus for determining the emphysema threshold and the apparatus for processing a pulmonary medical image may be stored in the non-volatile memory 630. Functionally, as shown in FIG. 7, the apparatus for determining the emphysema threshold may include a lung lobe region determination module 710, a lung lobe region division module 720, and a threshold determination module 730.

The lung lobe region determination module 710 is configured to determine lung lobe regions in a pulmonary medical image.

The lung lobe region division module 720 is configured, with respect to each of the lung lobe regions, to cluster CT values in the lung lobe region to divide the lung lobe region into a first sub region and a second sub region.

The threshold determination module 730 is configured, with respect to each of the lung lobe regions, to acquire a CT value corresponding to an intersection of a first CT value distribution function for the first sub region and a second CT value distribution function for the second sub region in the lung lobe region as an emphysema threshold for the lung lobe region.

In an example, the lung lobe region determination module 710 may include: a lung parenchymal region extraction sub-module configured to extract a lung parenchymal region from the pulmonary medical image; a lung parenchymal region division sub-module configured to divide the lung parenchymal region into a left lung region and a right lung region; a fissure point determination sub-module configured to determine lung lobe fissure points in the left lung region and the right lung region; and a lung lobe region division sub-module configured to construct a lung lobe fissure surface from the determined lung lobe fissure points, and determine each of the lung lobe regions in the pulmonary medical image based on the lung lobe fissure surface.

In another example, the lung lobe region division module 720 may be configured to: with respect to each of pixels in the lung lobe region, substitute the CT value of the pixel into a probability density function of a Gaussian Mixture Model to calculate a first probability and a second probability of the pixel, wherein the first probability represents a probability that the pixel belongs to a predetermined first classification, and the second probability represents a probability that the pixel belongs to a predetermined second classification; with respect to each of the pixels in the lung lobe region, to classify the pixel into a classification indicated by a higher one from the first possibility and the second possibility of this pixel; determine a region formed by pixels classified into the first classification as the first sub region of the lung lobe region; and determine a region formed by pixels classified into the second classification as the second sub region of the lung lobe region.

In another example, the threshold determination module 730 may be configured to acquire the first CT value distribution function based on CT values in the first sub region of the lung lobe region and predetermined distribution function values of the CT values; acquire the second CT value distribution function based on CT values in the second sub region of the lung lobe region and predetermined distribution function values of the CT values; calculate the intersection of the first CT value distribution function and the second CT value distribution function; and use an abscissa value of the intersection as the emphysema threshold for the lung lobe region.

As an example, both of the first CT value distribution function and the second CT value distribution function are probability density functions in a Gaussian Mixture Model.

Figure 8:
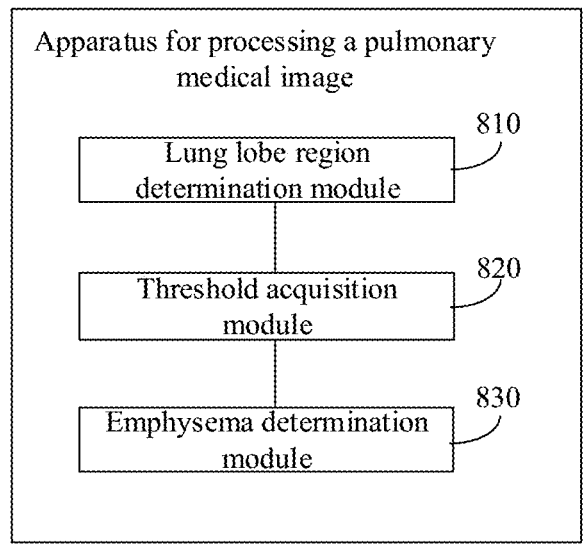
FIG. 8 is a block diagram showing an apparatus for processing a pulmonary medical image according to one or more examples of the present application.

As shown in FIG. 8, the apparatus for processing a pulmonary medical image may include a lung lobe region determination module 810, a threshold acquisition module 820, and an emphysema determination module 830.

The lung lobe region determination module 810 is configured to determine lung lobe regions in a pulmonary medical image.

The threshold acquisition module 820 is configured, with respect to each of the lung lobe regions, to acquire an emphysema threshold for the lung lobe region, wherein the emphysema threshold is a CT value corresponding to an intersection of a first CT value distribution function for a first sub region and a second CT value distribution function for a second sub region in the lung lobe region, and the first sub region and the second sub region are obtained by clustering CT values in the lung lobe region.

The emphysema determination module 830 is configured, with respect to each of the lung lobe regions, to determine a candidate emphysema region in the lung lobe region according to the emphysema threshold for the lung lobe region.

In an example, the emphysema determination module 830 may be further configured to determine a part of the lung lobe region having CT values smaller than the emphysema threshold for the lung lobe region as a candidate emphysema region of the lung lobe region.

In another example, the threshold acquisition module 820 may include: a lung lobe region division sub-module configured, with respect to each of the lung lobe regions, to cluster CT values in the lung lobe region to divide the lung lobe region into the first sub region and the second sub region; and a threshold determination sub-module configured, with respect to each of the lung lobe regions, to acquire the CT value corresponding to the intersection of the first CT value distribution function for the first sub region and the second CT value distribution function for the second sub region in the lung lobe region as the emphysema threshold for the lung lobe region.

As an example, the lung lobe region division sub-module is configured to: with respect to each of pixels in the lung lobe region, substitute the CT value of the pixel into a probability density function of a Gaussian Mixture Model to calculate a first probability and a second probability of the pixel, wherein the first probability represents a probability that the pixel belongs to a predetermined first classification, and the second probability represents a probability that the pixel belongs to a predetermined second classification; with respect to each of the pixels in the lung lobe region, classify the pixel into a classification indicated by a higher one from the first possibility and the second possibility of this pixel; determine a region formed by pixels classified into the first classification as the first sub region of the lung lobe region; and determine a region formed by pixels classified into the second classification as the second sub region of the lung lobe region.

As an example, the threshold determination sub-module is configured to acquire the first CT value distribution function based on CT values in the first sub region of the lung lobe region and predetermined distribution function values of the CT values; acquire the second CT value distribution function based on CT values in the second sub region of the lung lobe region and predetermined distribution function values of the CT values; calculate the intersection of the first CT value distribution function and the second CT value distribution function; and use an abscissa value of the intersection as the emphysema threshold for the lung lobe region.

As an example, both the first CT value distribution function and the second CT value distribution function are probability density functions in the Gaussian Mixture Model.

In some examples, the apparatus for processing a pulmonary medical image according to the examples of the present application may further include an emphysema screening module configured to optimize the candidate emphysema region using a pre-trained big data analysis model.

In some examples, the apparatus for processing a pulmonary medical image according to the examples of the present application may further include: an emphysema marking module configured to mark determined candidate emphysema regions on the pulmonary medical image; and an emphysema parameter calculation module configured to calculate at least one of the following emphysema parameters according to the determined candidate emphysema regions: position coordinates of each candidate emphysema region; a volume of each candidate emphysema region; a surface area of each candidate emphysema region; and an air content of lung.

In some examples, the apparatus for processing a pulmonary medical image may further include a lung parameter calculation module configured to calculate at least one of the following lung parameters according to the pulmonary medical image: a pulmonary CT mean, a lung volume, a lung surface area, a pulmonary tissue volume, a pulmonary tissue weight, a pulmonary tissue density, a left lung volume, a right lung volume, and a pulmonary trachea volume.

The terms used in the present application are only for the purpose of describing particular examples, but is not intended to be restrictive. Singular forms "a", "an", and "the" used in the present application and appended claims mean inclusion of plural forms unless the context thereof indicates other meanings. It should be understood that the term "and/or" as used herein refers to and encompasses any or all possible combinations of one or more of associated listed items.

For realization of functions and effects of various units (or modules) in the apparatuses of the examples, please refer to the description of the examples of the corresponding methods, which will not be described herein again.

Other examples of the present application will be readily apparent to those skilled in the art after considering the specification and practicing the contents disclosed herein. The present application is intended to cover any variations, uses, or adaptations of the present application, which follow the general principles of the present application and include the common knowledge or conventional technical means in the art that are not disclosed in the present application. The specification and examples are to be regarded as illustrative only. The true scope and spirit of the present application is pointed out by the appended claims.

It should be understood that the present application is not limited to the precise structures that have been described above and illustrated in the drawings, and various modifications and changes can be made without departing from the scope thereof. The scope of the present application is to be limited only by the appended claims.

What is claimed is:

1. A method of determining emphysema thresholds for processing a pulmonary medical image, the method comprising:

determining lung lobe regions in the pulmonary medical image; and for each of the lung lobe regions, clustering CT values in the lung lobe region to divide the lung lobe region into a first sub region and a second sub region, wherein one of the first sub region and the second sub region represents a healthy tissue region, and the other one of the first sub region and the second sub region represents a region where an emphysema lesion is potentially contained, and acquiring a CT value corresponding to an intersection of a first CT value distribution function for the first sub region and a second CT value distribution function for the second sub region in the lung lobe region as an emphysema threshold for the lung lobe region, wherein clustering the CT values in the lung lobe region to divide the lung lobe region into the first sub region and the second sub region comprises:

for each of pixels in the lung lobe region, substituting a CT value of the pixel into a probability density function of a Gaussian Mixture Model to calculate a first probability and a second probability of the pixel, wherein the first probability represents a probability that the pixel belongs to a predetermined first classification, and the second probability represents a probability that the pixel belongs to a predetermined second classification, and classifying the pixel into a classification indicated by a higher one of the first probability and the second probability;

determining a region formed by pixels classified into the predetermined first classification as the first sub region of the lung lobe region; and determining a region formed by pixels classified into the predetermined second classification as the second sub region of the lung lobe region.

2. The method of claim 1, wherein acquiring the CT value corresponding to the intersection of the first CT value distribution function for the first sub region and the second CT value distribution function for the second sub region in the lung lobe region as the emphysema threshold for the lung lobe region comprises:

acquiring the first CT value distribution function based on CT values in the first sub region of the lung lobe region and predetermined distribution function values of the CT values;

acquiring the second CT value distribution function based on CT values in the second sub region of the lung lobe region and predetermined distribution function values of the CT values;

calculating the intersection of the first CT value distribution function and the second CT value distribution function; and determining an abscissa value of the intersection as the emphysema threshold for the lung lobe region.

3. The method of claim 1, wherein both of the first CT value distribution function and the second CT value distribution function are probability density functions in a Gaussian Mixture Model.

4. The method of claim 1, wherein determining the lung lobe regions in the pulmonary medical image comprises:

extracting a lung parenchymal region from the pulmonary medical image;

dividing the lung parenchymal region into a left lung region and a right lung region;

determining lung lobe fissure points in the left lung region and the right lung region;

constructing a lung lobe fissure surface from the determined lung lobe fissure points; and determining each of the lung lobe regions in the pulmonary medical image based on the lung lobe fissure surface.

5. The method of claim 4, wherein determining the lung lobe fissure points in the left lung region and the right lung region comprises:

performing Gaussian filtering on the left lung region and the right lung region;

suppressing at least one of local fissure bright spots, blood vessel wall signal points, fissure points near blood vessel walls, or non-planar and non-curved fissure points in the filtered left lung region and right lung region, to obtain a processed left lung region and right lung region; and extracting the lung lobe fissure points from the processed left lung region and right lung region.

6. A method of processing a pulmonary medical image, the method comprising:

determining lung lobe regions in the pulmonary medical image; and for each of the lung lobe regions, acquiring an emphysema threshold for the lung lobe region, wherein the emphysema threshold is a CT value corresponding to an intersection of a first CT value distribution function for a first sub region of the lung lobe region and a second CT value distribution function for a second sub region of the lung lobe region, the first sub region and the second sub region being obtained by clustering CT values in the lung lobe region to divide the lung lobe region into the first sub region and the second sub region, one of the first sub region and the second sub region representing a healthy tissue region, and the other one of the first sub region and the second sub region representing a region where an emphysema lesion is potentially contained, and determining a candidate emphysema region in the lung lobe region according to the emphysema threshold for the lung lobe region, wherein clustering the CT values in the lung lobe region to divide the lung lobe region into the first sub region and the second sub region comprises:

for each of pixels in the lung lobe region, substituting a CT value of the pixel into a probability density function of a Gaussian Mixture Model to calculate a first probability and a second probability of the pixel, wherein the first probability represents a probability that the pixel belongs to a predetermined first classification, and the second probability represents a probability that the pixel belongs to a predetermined second classification, and classifying the pixel into a classification indicated by a higher one from the first probability and the second probability;

determining a region formed by pixels classified into the predetermined first classification as the first sub region of the lung lobe region; and determining a region formed by pixels classified into the predetermined second classification as the second sub region of the lung lobe region.

7. The method of claim 6, wherein determining the candidate emphysema region in the lung lobe region according to the emphysema threshold for the lung lobe region comprises:

determining a part of the lung lobe region having CT values smaller than the emphysema threshold for the lung lobe region as the candidate emphysema region in the lung lobe region.

8. The method of claim 6, wherein both of the first CT value distribution function and the second CT value distribution function are probability density functions in a Gaussian Mixture Model.

9. The method of claim 6, wherein acquiring the emphysema threshold for the lung lobe region comprises:

acquiring the CT value corresponding to the intersection of the first CT value distribution function for the first sub region and the second CT value distribution function for the second sub region in the lung lobe region as the emphysema threshold for the lung lobe region.

10. The method of claim 9, wherein acquiring the CT value corresponding to the intersection of the first CT value distribution function for the first sub region and the second CT value distribution function for the second sub region in the lung lobe region as the emphysema threshold for the lung lobe region comprises:
    acquiring the first CT value distribution function based on CT values in the first sub region of the lung lobe region and predetermined distribution function values of the CT values;
    acquiring the second CT value distribution function based on CT values in the second sub region of the lung lobe region and predetermined distribution function values of the CT values;
    calculating the intersection of the first CT value distribution function and the second CT value distribution function; and
    determining an abscissa value of the intersection as the emphysema threshold for the lung lobe region.

11. The method of claim 6, further comprising:
    optimizing the candidate emphysema region using a pre-trained big data analysis model.

12. The method of claim 11, wherein the pulmonary medical image is associated with a region of interest of a subject, and
    wherein the pre-trained big data analysis model is trained by samples comprising a plurality of pulmonary medical images obtained from multiple CT scans of the same region of interest of multiple subjects and corresponding emphysema thresholds for the plurality of pulmonary medical images.

13. A computing device for processing a pulmonary medical image, the device comprising:
    at least one processor; and
    at least one non-transitory machine readable storage medium coupled to the at least one processor having machine-executable instructions stored thereon that, when executed by the at least one processor, cause the at least one processor to perform operations comprising:
        determining lung lobe regions in the pulmonary medical image; and
        for each of the lung lobe regions,
            acquiring an emphysema threshold for the lung lobe region, wherein the emphysema threshold is a CT value corresponding to an intersection of a first CT value distribution function for a first sub region and a second CT value distribution function for a second sub region in the lung lobe region, and the first sub region and the second sub region are obtained by clustering CT values in the lung lobe region to divide the lung lobe region into the first sub region and the second sub region, one of the first sub region and the second sub region representing a healthy tissue region, and the other one of the first sub region and the second sub region representing a region where an emphysema lesion is potentially contained, and
            determining a candidate emphysema region in the lung lobe region according to the emphysema threshold for the lung lobe region,
    wherein clustering the CT values in the lung lobe region to divide the lung lobe region into the first sub region and the second sub region comprises:
        for each of pixels in the lung lobe region,
            substituting a CT value of the pixel into a probability density function of a Gaussian Mixture Model to calculate a first probability and a second probability of the pixel, wherein the first probability represents a probability that the pixel belongs to a predetermined first classification, and the second probability represents a probability that the pixel belongs to a predetermined second classification, and
            classifying the pixel into a classification indicated by a higher one from the first probability and the second probability;
        determining a region formed by pixels classified into the predetermined first classification as the first sub region of the lung lobe region; and
        determining a region formed by pixels classified into the predetermined second classification as the second sub region of the lung lobe region.

14. The device of claim 13, wherein determining the candidate emphysema region in the lung lobe region according to the emphysema threshold for the lung lobe region comprises:
    determining a part of the lung lobe region having CT values smaller than the emphysema threshold for the lung lobe region as the candidate emphysema region in the lung lobe region.

15. The device of claim 13, wherein determining the lung lobe regions in the pulmonary medical image comprises:
    extracting a lung parenchymal region from the pulmonary medical image;
    dividing the lung parenchymal region into a left lung region and a right lung region;
    determining lung lobe fissure points in the left lung region and the right lung region;
    constructing a lung lobe fissure surface from the determined lung lobe fissure points; and
    determining each of the lung lobe regions in the pulmonary medical image based on the lung lobe fissure surface, and
    wherein determining the lung lobe fissure points in the left lung region and the right lung region comprises:
    performing Gaussian filtering on the left lung region and the right lung region;
    suppressing local fissure bright spots, blood vessel wall signal points, fissure points near blood vessel walls, and non-planar and non-curved fissure points in the filtered left lung region and right lung region, to obtain a processed left lung region and right lung region; and
    extracting the lung lobe fissure points from the processed left lung region and right lung region.

16. The device of claim 13, wherein acquiring the emphysema threshold for the lung lobe region comprises:
    acquiring the CT value corresponding to the intersection of the first CT value distribution function for the first sub region and the second CT value distribution function for the second sub region in the lung lobe region as the emphysema threshold for the lung lobe region.

17. The device of claim 16, wherein acquiring the CT value corresponding to the intersection of the first CT value distribution function for the first sub region and the second CT value distribution function for the second sub region in the lung lobe region as the emphysema threshold for the lung lobe region comprises:
    acquiring the first CT value distribution function based on CT values in the first sub region of the lung lobe region and predetermined distribution function values of the CT values;
    acquiring the second CT value distribution function based on CT values in the second sub region of the lung lobe region and predetermined distribution function values of the CT values;

calculating the intersection of the first CT value distribution function and the second CT value distribution function; and determining an abscissa value of the intersection as the emphysema threshold for the lung lobe region.

* * * * *